(12) United States Patent
Callister

(10) Patent No.: US 11,717,430 B2
(45) Date of Patent: *Aug. 8, 2023

(54) METHOD AND SYSTEM FOR DELIVERING A SELF-EXPANDING STENT TO THE VENOUS SINUSES

(71) Applicant: Serenity Medical, Inc., Deephaven, MN (US)

(72) Inventor: Jeffrey P. Callister, Deephaven, MN (US)

(73) Assignee: Serenity Medical, Inc., Deephaven, MN (US)

( * ) Notice: Subject to any disclaimer, the term of this patent is extended or adjusted under 35 U.S.C. 154(b) by 181 days.

This patent is subject to a terminal disclaimer.

(21) Appl. No.: 17/193,193

(22) Filed: Mar. 5, 2021

(65) Prior Publication Data

US 2022/0023079 A1 Jan. 27, 2022

Related U.S. Application Data

(63) Continuation of application No. 15/456,352, filed on Mar. 10, 2017, now Pat. No. 10,940,030.

(51) Int. Cl.
*A61F 2/966* (2013.01)
*A61F 2/915* (2013.01)
(Continued)

(52) U.S. Cl.
CPC .............. *A61F 2/966* (2013.01); *A61F 2/915* (2013.01); *A61F 2/9517* (2020.05);
(Continued)

(58) Field of Classification Search
CPC ................................ A61F 2/915; A61F 2/966
See application file for complete search history.

(56) References Cited

U.S. PATENT DOCUMENTS

| 5,192,289 A | 3/1993 | Jessen |
| 5,222,965 A | 6/1993 | Haughton |

(Continued)

FOREIGN PATENT DOCUMENTS

| CN | 102227194 A | 10/2011 |
| CN | 102753119 A | 10/2012 |

(Continued)

OTHER PUBLICATIONS

Pierce, Damon S. et al., "Open-cell versus closed-cell stent design differences in blood flow velocities after carotid stenting," Journal of Vascular Surgery, vol. 49, No. 3, Mar. 2009, pp. 602-606.

(Continued)

*Primary Examiner* — Sarah A Long
(74) *Attorney, Agent, or Firm* — McAndrews, Held & Malloy, Ltd.

(57) ABSTRACT

A stent delivery system includes a shaft extending from a proximal end of the system into a delivery tip at a distal end. The shaft includes a coil and a stent bed. A stent is loaded onto the stent bed and has a first portion at its distal end having a greater flexibility than a second portion at its proximal end. Sheathing is movable over the stent bed between pre-deployed and deployed positions. The sheathing includes a flexible section at the sheathing distal end, a semi-flexible section adjacent the flexible section, and a stiff section adjacent the semi-flexible section. The delivery tip is more flexible than the combination of the stent bed, the first portion of the stent, and the flexible section of the sheathing, which is more flexible than the combination of the stent bed, the second portion the stent, and the flexible section of the sheathing.

19 Claims, 9 Drawing Sheets

(51) Int. Cl.
    *A61F 2/82*        (2013.01)
    *A61F 2/95*        (2013.01)
(52) U.S. Cl.
    CPC .............. *A61F 2002/825* (2013.01); *A61F 2002/91575* (2013.01); *A61F 2230/0067* (2013.01); *A61F 2230/0069* (2013.01); *A61F 2250/0029* (2013.01); *A61F 2250/0039* (2013.01)

(56) References Cited

U.S. PATENT DOCUMENTS

| | | | |
|---|---|---|---|
| 5,649,952 | A | 7/1997 | Lam |
| 5,713,917 | A | 2/1998 | Leonhardt et al. |
| 5,902,332 | A | 5/1999 | Schatz |
| 5,938,697 | A | 8/1999 | Killion |
| 6,019,778 | A | 2/2000 | Wilson et al. |
| 6,702,802 | B1 | 3/2004 | Hancock et al. |
| 6,706,061 | B1 | 3/2004 | Fischell et al. |
| 6,743,252 | B1 | 6/2004 | Bates et al. |
| 7,172,623 | B2 | 2/2007 | Hansen et al. |
| 7,828,832 | B2 * | 11/2010 | Belluche ............. A61F 2/966 623/1.11 |
| 7,867,271 | B2 | 1/2011 | Geiser et al. |
| 2001/0010013 | A1 | 7/2001 | Cox et al. |
| 2003/0040789 | A1 | 2/2003 | Colgan et al. |
| 2003/0212410 | A1 | 11/2003 | Stenzel et al. |
| 2004/0267350 | A1 | 12/2004 | Roubin et al. |
| 2005/0149168 | A1 | 7/2005 | Gregorich |
| 2006/0235502 | A1 | 10/2006 | Belluche et al. |
| 2008/0051876 | A1 | 2/2008 | Ta et al. |
| 2008/0221661 | A1 | 9/2008 | Bidne et al. |
| 2009/0149935 | A1 | 6/2009 | Chu et al. |
| 2012/0226343 | A1 | 9/2012 | Vo et al. |
| 2012/0271408 | A1 | 10/2012 | Colgan et al. |
| 2015/0032198 | A1 | 1/2015 | Folk |
| 2015/0081000 | A1 | 3/2015 | Hossainy et al. |
| 2015/0196741 | A1 * | 7/2015 | Heilman ............. A61B 90/39 604/9 |
| 2015/0265438 | A1 * | 9/2015 | Hossainy ............. A61L 31/041 623/1.11 |
| 2016/0074189 | A1 * | 3/2016 | Cummins ............. A61F 2/966 623/1.11 |
| 2016/0206452 | A1 | 7/2016 | Berez et al. |
| 2016/0256306 | A1 * | 9/2016 | Cindrich ............. A61F 2/844 |
| 2017/0000311 | A1 | 1/2017 | Kamagata et al. |
| 2017/0035592 | A1 | 2/2017 | Haggstrom et al. |

FOREIGN PATENT DOCUMENTS

| | | |
|---|---|---|
| CN | 102764165 A | 11/2012 |
| CN | 103118630 A | 5/2013 |
| CN | 103458832 A | 12/2013 |
| CN | 104042378 A | 9/2014 |
| EP | 1181906 A2 | 2/2002 |
| EP | 1707233 A2 | 10/2006 |
| EP | 1716822 | 11/2006 |
| EP | 2263618 A1 | 2/2010 |
| JP | 2002505149 | 2/2002 |
| JP | 2009523543 A | 6/2009 |
| WO | 9116005 A1 | 10/1991 |
| WO | 9518585 A1 | 7/1995 |
| WO | 9943379 A1 | 9/1999 |
| WO | 9949812 | 10/1999 |
| WO | 0156505 A | 8/2001 |
| WO | 2004002371 A | 1/2004 |
| WO | 2007084547 A1 | 7/2007 |
| WO | 2012015825 A2 | 2/2012 |
| WO | 2015038875 A1 | 3/2015 |
| WO | 2019160758 | 8/2019 |

OTHER PUBLICATIONS

Stoecke, D., et al., "A survey of stent designs," Min Invas Ther & Allied Technol, vol. 11, No. 4, 2002, pp. 137-147.
Ahmed, et al., "Transverse Sinus Stenting for Idiopathic Intracranial Hypertension: A Review of 52 Patients and of Model Predictions," AJNR 32, www.ajnr.org, Sep. 2011, pp. 1408-1414.
Albuquerque, et al., "Intracranial Venous Sinus Stenting for Benign Intracranial Hypertension: Clinical Indications, Technique, and Preliminary Results," www.SCIENCEDIRECT.com, World Neurosurgery, 2010, 648-652.
Bussiere, et al., "Unilateral Transverse Sinus Stenting of Patients with Idiopathic Intracranial Hypertension," AJNR AM J Neuroradiol 31, www.ajnr.org, Apr. 2010, pp. 645-650.
Ducruet, et al., "Long-Term patency of venous sinus stents for idiopathic intracranial hypertension," J. NeuroIntervent Surg, 2013, pp. 1-5.
Fields, et al., "Dural venous sinus angioplasty and stenting for the treatment of idiopathic intracranial hypertension," J. NeuroIntervent Surg, 2013, pp. 62-68.
Higgins, et al., "Venous sinus stenting for refractory benign intracranial hypertension," The Lancet, vol. 359, Jan. 19, 2002, pp. 228-230.
Higgins, et al., "Idiopathic intracranial hypertension: 12 cases treated by venous sinus stenting," J. Neurol. Neurosurg. Psychiatry, 2003, pp. 1662-1666.
Kanagalingam, et al., "Cerebral venous sinus stenting for pseudotumor cerebri A review," Saudi Journal of Ophthalmology, 2015, vol. 29, pp. 3-8.
Kumpe, et al., "Dural sinus stent placement for idiopathic intracranial hypertension," J. Neurosurg, vol. 116, 2012, pp. 538-548.
Riggeal, et al., "Clinical course of idiopathic intracranial hypertension with transverse sinus stenosis," American Academy of Neurology, 2012, pp. 289-295.
Smith, et al., "A case series of dural venous sinus stenting in idiopathic intracranial hypertension: association of outcomes with optical coherence tomography," International Journal of Neuroscience, 2016, pp. 1-9.
Starke, et al., "Endovascular Treatment of Venous Sinus Stenosis in Idiopathic Intracranial Hypertension: Complications, Neurological Outcomes, and Radiographic Results," The Scientific World Journal, vol. 2015, Article ID 140408, pp. 1-8.
Teleb, et al., "Stenting and Angioplasty for Idiopathic Intracranial Hypertension: A Case Series with Clinical, Angiographic, Ophthalmological, Complication, and Pressure Reporting," American Society of NeuroImaging, 2013, pp. 72-80.
Tsumoto, et al., "Restenosis of the sigmoid sinus after stenting for treatment of intracranial venous hypertension: case report," Neuroradiology, 2003, vol. 45, pp. 911-915.
Winters, et al., "Delayed relapse in pseudotumor cerebri due to new stenosis after transverse sinus stenting," J. NeuroIntervent Surg, 2015, vol. 00, pp. 1-3.
International Search Report for International Application No. PCT/US18/21527, dated Jul. 12, 2018, 4 pages.
International Preliminary Report for International Application No. PCT/US18/21527, dated Sep. 19, 2019, 10 pages.
Search Report and Written Opinion issued from the Intellectual Property Office of Singapore (IPOS) for Patent Application No. 11201908318Q, dated Oct. 27, 2020, 7 pages.
Supplementary European Search Report issued from European Patent Office for Patent Application No. 18764232.7, dated Nov. 26, 2020, 9 pages.
Examination Report for Singapore Application No. 11201908318Q dated Jul. 1, 2022, pp. 1-4.
Preliminary Office Action for Brazilian Patent Application No. BR112019018668-9, Brazilian Property Journal No. 2697 of Sep. 13, 2022, 6 pages.
First Office Action issued in Chinese Patent Application No. 2018800209121 dated Apr. 19, 2021, 22 pages.
Search Report issued in Chinese Patent Application No. 2018800209121 dated Apr. 19, 2021, 3 pages.
Second Office Action issued in Chinese Patent Application No. 2018800209121 dated Dec. 7, 2021, 12 pages.

(56) References Cited

OTHER PUBLICATIONS

Office Action issued in Japanese Patent Application No. 2019-570346 dated Dec. 2, 2021, 13 pages.

* cited by examiner

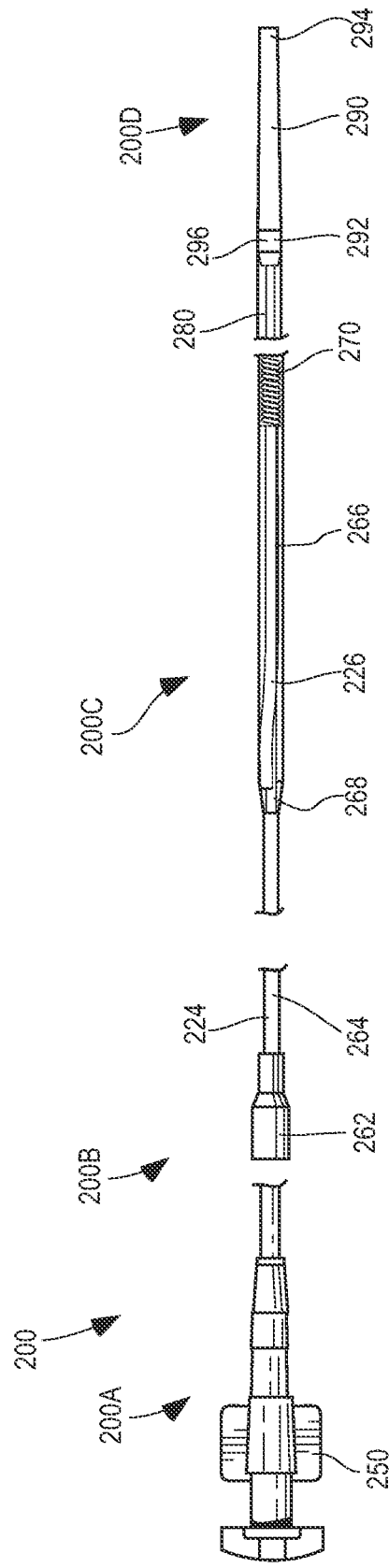

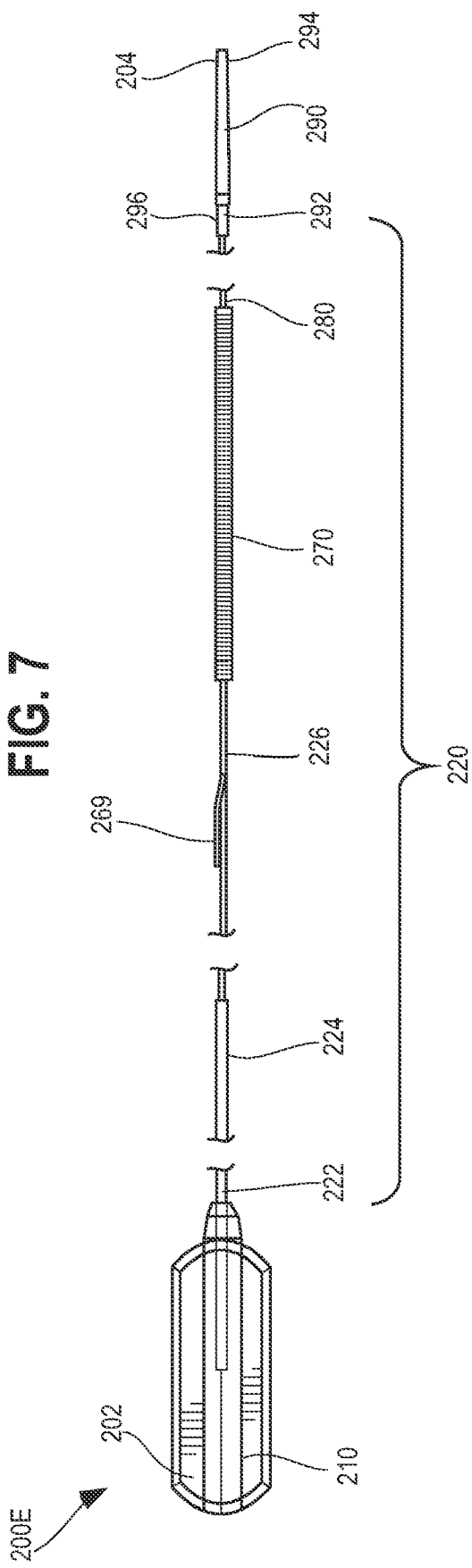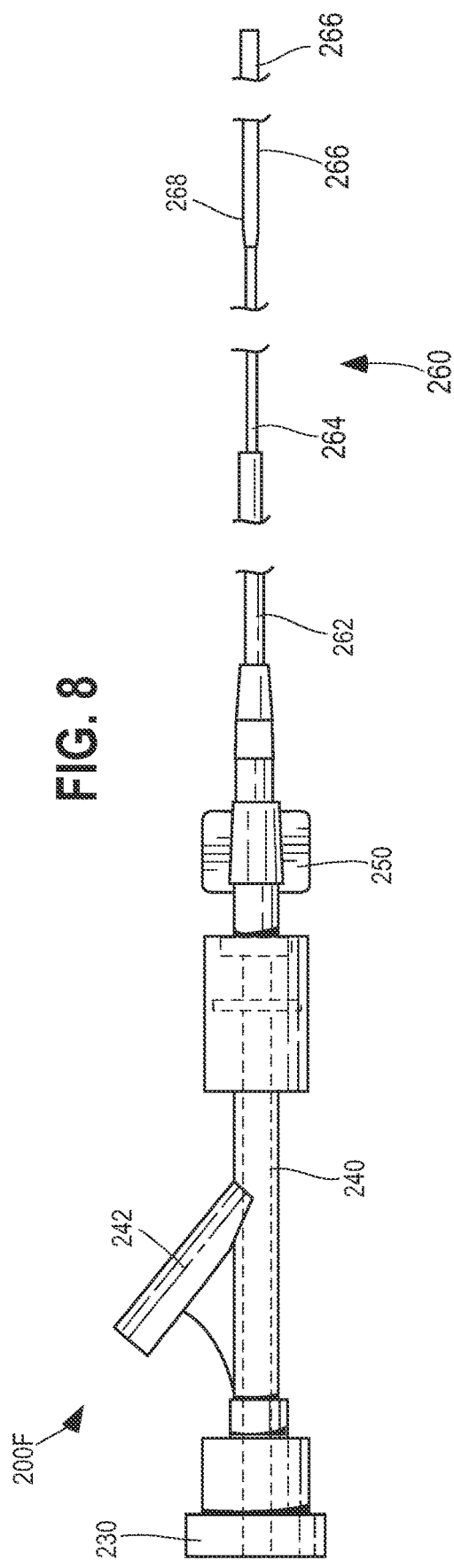

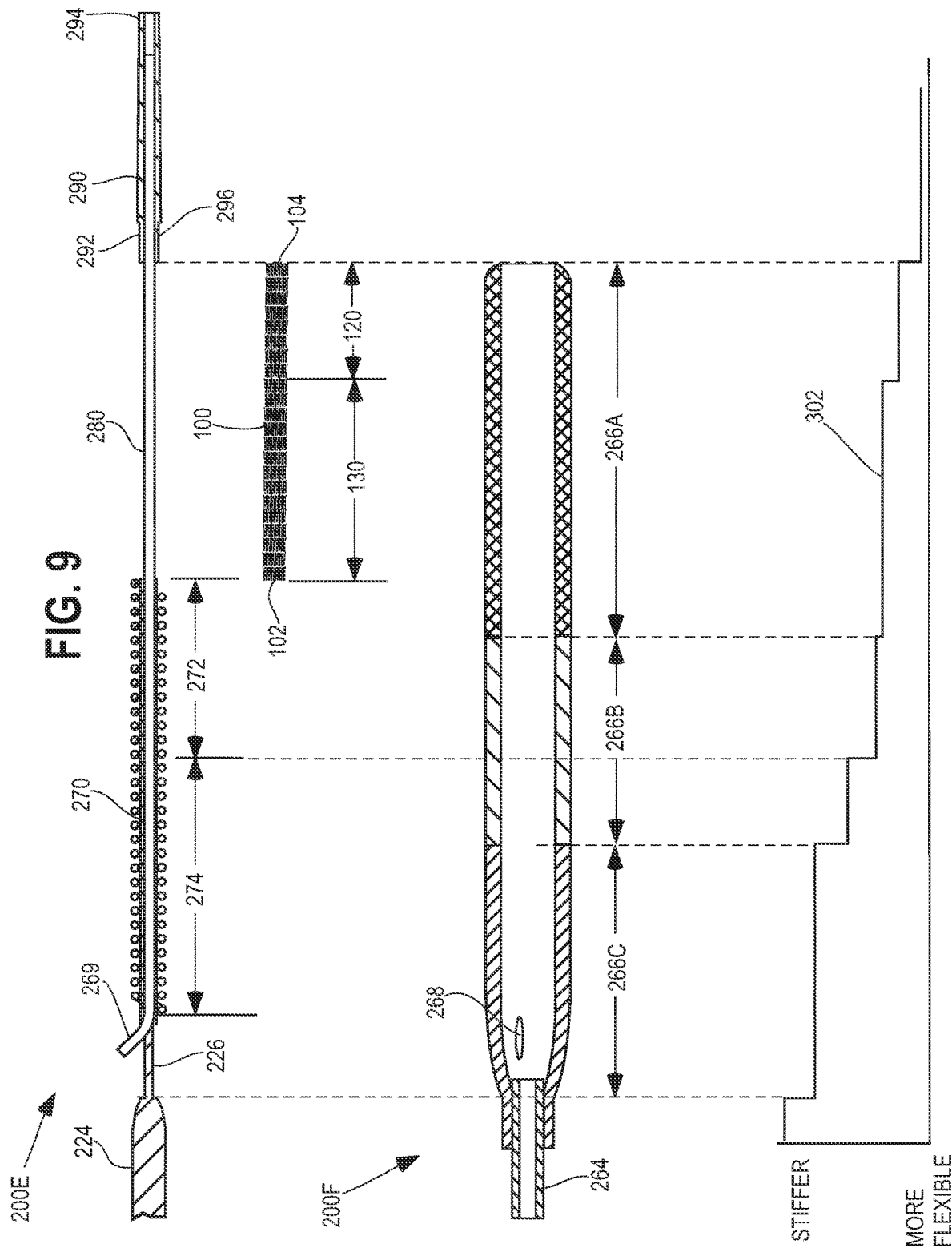

METHOD AND SYSTEM FOR DELIVERING A SELF-EXPANDING STENT TO THE VENOUS SINUSES

CROSS-REFERENCE TO RELATED APPLICATIONS/INCORPORATION BY REFERENCE

The present application is a continuation of U.S. patent application Ser. No. 15/456,352, filed Mar. 10, 2017, and titled "METHOD AND SYSTEM FOR DELIVERING A SELF-EXPANDING STENT TO THE VENOUS SINUSES," now U.S. Pat. No. 10,940,030, the entire contents of which are hereby incorporated herein by reference in their entirety.

FIELD

Certain embodiments relate to stents and systems and methods for delivering a stent. More specifically, certain embodiments relate to a method and system for treating a stenosis or collapse in the venous sinuses by delivering a self-expanding stent. In various embodiments, the self-expanding stent comprises a proximal end having a first radial outward expansion strength (RES) that is greater than a second RES at a distal end of the stent. In a representative embodiment, the proximal end of the stent comprises a diameter that is greater than the diameter at the distal end of the stent. In certain embodiments, the flexibility of the stent delivery system and/or the stent increases from the proximal end toward the distal end of the system and/or stent.

BACKGROUND

When blood exiting the brain is slowed by a restriction in the venous sinuses, it causes an increase to the distal blood pressure, which may translate to an increase in the brain fluid pressure. Patients experiencing Increased Intracranial Pressure (ICP), where the Cerebral Spinal Fluid (CSF) pressure in the cranium has increased, may suffer from headaches, loss of vision, and/or tinnitus, among other things. The preferred method for treating a collapse of and/or a stenosis in the sigmoid and/or transverse sinus has been drugs and/or using a shunt to relieve the CSF fluid pressure. The use of drugs or a shunt is not ideal, however, because both are temporary solutions that each carry associated risks.

More, recently, a new procedure has been carried out that involves placing a stent in the venous sinus system of patients to ameliorate a collapse of and/or a stenosis in the sigmoid and/or transverse sinus and to restore improved blood flow out of the brain. The stent used in the new procedure typically is the same stent used for procedures in other parts of the body, such as the carotid artery. The venous sinus structure, however, does not resemble any vein or arteries of other parts of the body. Instead, the venous sinus is a void created where the dura joins and forms a cavity (i.e., sinus) primarily along the inside of the skull. The dura has no smooth muscle cell lining and is inelastic when compared to veins and arteries.

FIG. 1 illustrates an exemplary venous sinus system having an identified stent zone. The venous sinus system comprises venous channels found between the periosteal and meningeal layers of dura mater in the brain. The venous sinus system receives blood from internal and external veins of the brain, receives CSF from the subarachnoid space via arachnoid granulations, and mainly empties into the internal jugular vein. As illustrated in FIG. 1, the venous sinus system includes the transverse sinus, sigmoid sinus, and the sigmoid junction. The sigmoid sinus integrates into the jugular vein at the sigmoid junction. FIG. 1 also identifies an exemplary stent zone for placing a stent to treat a collapse of and/or a stenosis in the sigmoid and/or transverse sinus.

Existing stent delivery systems and stents have several inadequacies for delivering a stent to the venous sinuses. For example, existing stents and systems may be incapable of or difficult to navigate through the tortuous sigmoid junction for placement of the stent in the stent zone.

As another example, the properties of existing stents may be undesirable for placement in the venous sinuses. The length of a typical carotid artery stent may be 4-6 cm long. However, after placement of a carotid artery stent in the venous sinuses, a portion of the transverse sinus could collapse, particularly a portion that is distal to the distal end of the stent. The collapse of a portion of the transverse sinus may occur if the stent is placed in the sigmoid to transverse junction and is not long enough to scaffold most or the entirety of transverse sinus. Additionally, multiple carotid artery stents may be required if there are collapses and/or stenosis at multiple locations in the sigmoid and/or transverse sinuses. Also, a stent having an inappropriate length could be incorrectly positioned at the curves in the sigmoid sinus to block off future access to the sinus (e.g., a stent jail). For example, a stent that terminates within a curve, instead of being positioned through the curve, may block a portion or the entire sinus lumen at the curve.

Furthermore, exiting stents typically come in one set diameter. However, the middle and distal region of the sigmoid sinus has on average a larger diameter (e.g., ~10-12 mm) than the distal section of the transverse sinus (e.g., ~6-9 mm). Accordingly, existing stent diameters positioned in both the sigmoid and transverse sinuses may be inadequate for at least one of the sinuses. For example, if the stent is too small for a vessel, a portion of the stent can be left dangling or free floating in the vessel, which may prevent proper endothelium tissue growth over the stent struts. As another example, if the stent is too large for a vessel, various problems may occur because the radial outward expansion strength (RES) of typical stents may be too forceful for use in the venous sinuses. Specifically, stents intended for placement in large vessels such as the carotid artery, femoral artery or veins, and the like, may have a high RES required for treatment of occlusions, atherosclerosis plaque, and lesion calcification, and/or that can withstand an outside force capable of pushing in on the stent. This high RES, coupled with a stent size that is too large for a vessel, can create a problem of tissue in contact with the stent struts dying due to the strong outward pressure exerted on the tissue. Another problem arising with a high RES when stents are too large for a vessel is that the stent may push through the vessel wall and show on the outside of the vessel.

Existing stent designs may also have an abundance of struts members. However, the venous sinus structure includes numerous small veins leading from the brain. Accordingly, the quantity of strut members of a typical stent increases the chance that one strut might block, or partially inhibit the venous inflow from the brain via the veins.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY

Enhanced navigation of a stent delivery system for placement of a stent is provided by increasing the flexibility of the stent delivery system and/or the stent from the proximal end toward the distal end of the system and/or stent, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

BRIEF DESCRIPTION OF SEVERAL VIEWS OF THE DRAWINGS

FIG. 6 illustrates a detail view of portions of the exemplary stent delivery system of FIG. 5, in accordance with various embodiments.

FIG. 7 illustrates a detail view of an inner portion of the stent delivery system of FIG. 5, in accordance with various embodiments.

FIG. 8 illustrates a detail view of an outer portion of the stent delivery system of FIG. 5, in accordance with various embodiments.

FIG. 9 illustrates an exploded, cross-sectional view of the inner portion of the stent delivery system, the stent, and the outer portion of the stent delivery system, where the increasing flexibility of the stent delivery system with the stent from the proximal end toward the distal end of the system and stent is illustrated by a mapping to an exemplary flexibility chart, in accordance with various embodiments.

DETAILED DESCRIPTION

Figure 1:
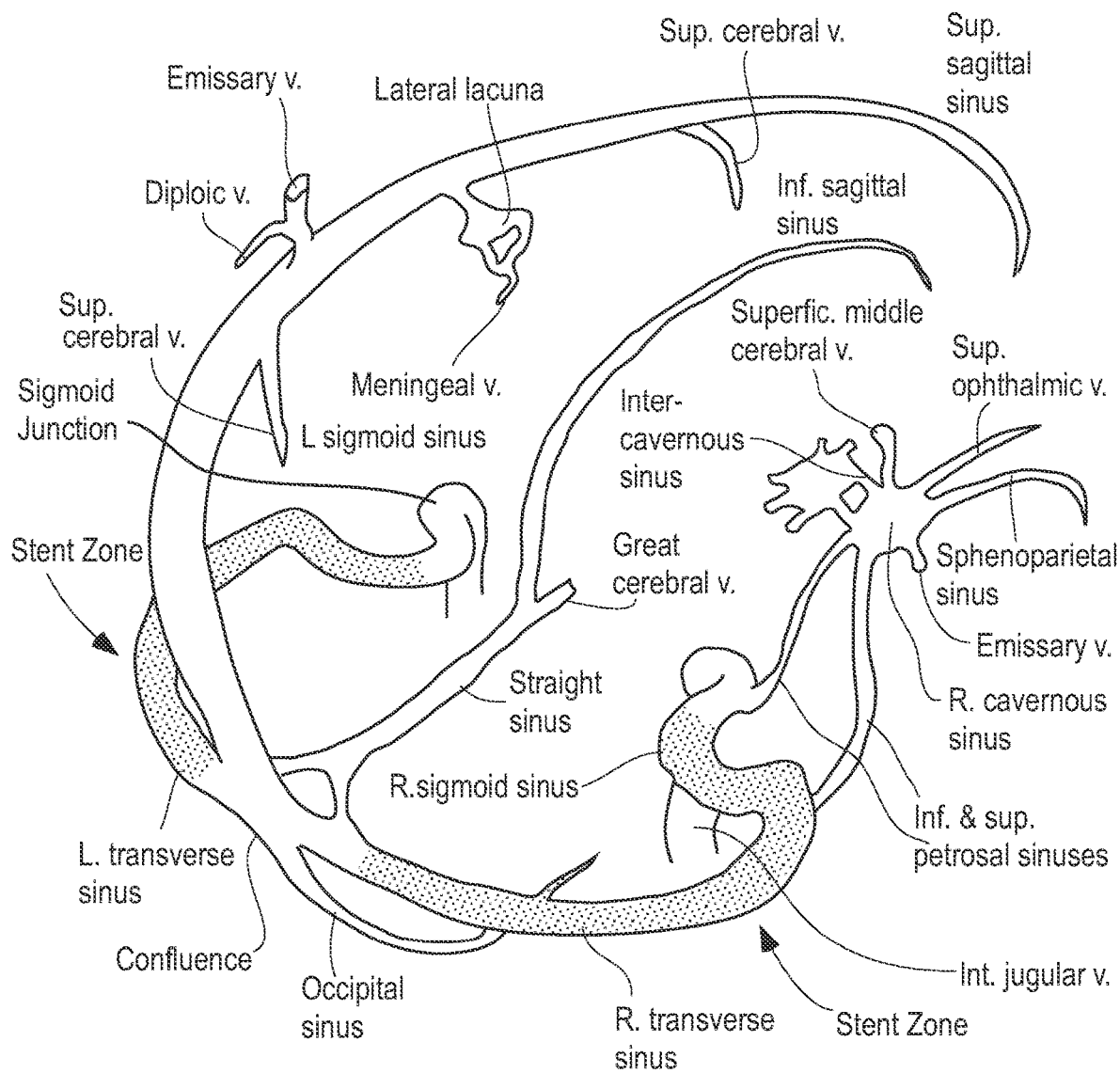
FIG. 1 illustrates an exemplary venous sinus system having an identified stent zone, in accordance with various embodiments.

Certain embodiments may provide enhanced navigation of a stent delivery system for placement of a stent by increasing the flexibility of the stent delivery system and/or the stent from the proximal end toward the distal end of the system and/or stent. Various embodiments provide a self-expanding stent that comprises a proximal end having a first radial outward expansion strength (RES) that is greater than a second RES at a distal end of the stent. In a representative embodiment, the proximal end of the stent comprises a diameter that is greater than the diameter at the distal end of the stent. In certain embodiments, the stent delivery system may be configured to treat a stenosis or collapse in the venous sinuses by delivering the self-expanding stent.

The foregoing summary, as well as the following detailed description of certain embodiments will be better understood when read in conjunction with the appended drawings. It should be understood that the various embodiments are not limited to the arrangements and instrumentality shown in the drawings. It should also be understood that the embodiments may be combined, or that other embodiments may be utilized and that structural changes may be made without departing from the scope of the various embodiments. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property. As referred to herein, the terms "proximal" and "distal" are in relation to the delivery handle 210 of the stent delivery system 200 (also referred to as a catheter). For example, the distal end 104, 204 of the stent 100 and the catheter 200 is the end that is inserted first into a body lumen of a patient and the proximal end 102, 204 is opposite the distal end 104, 204.

Figure 2:
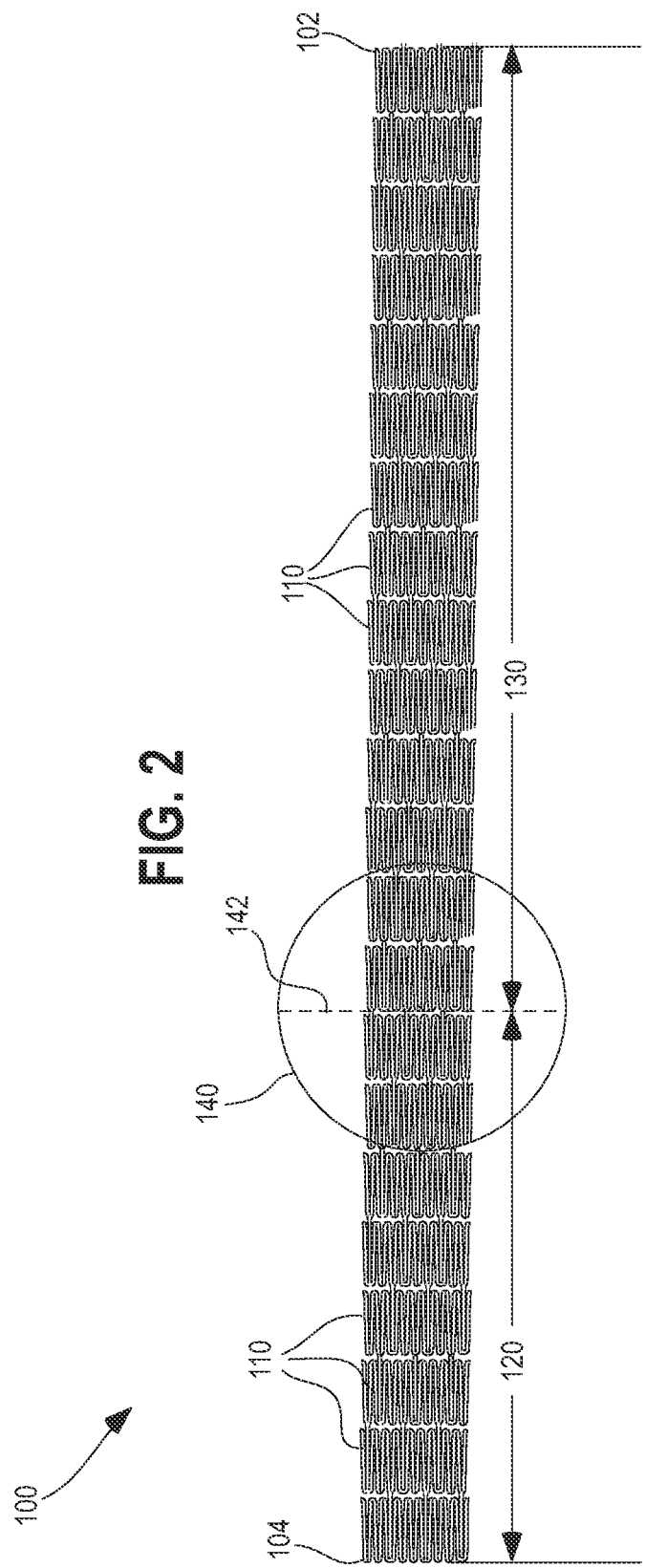
FIG. 2 illustrates an exemplary stent comprising a distal end and a proximal end, the distal end having a greater flexibility than the proximal end, in accordance with various embodiments.
Figure 3:
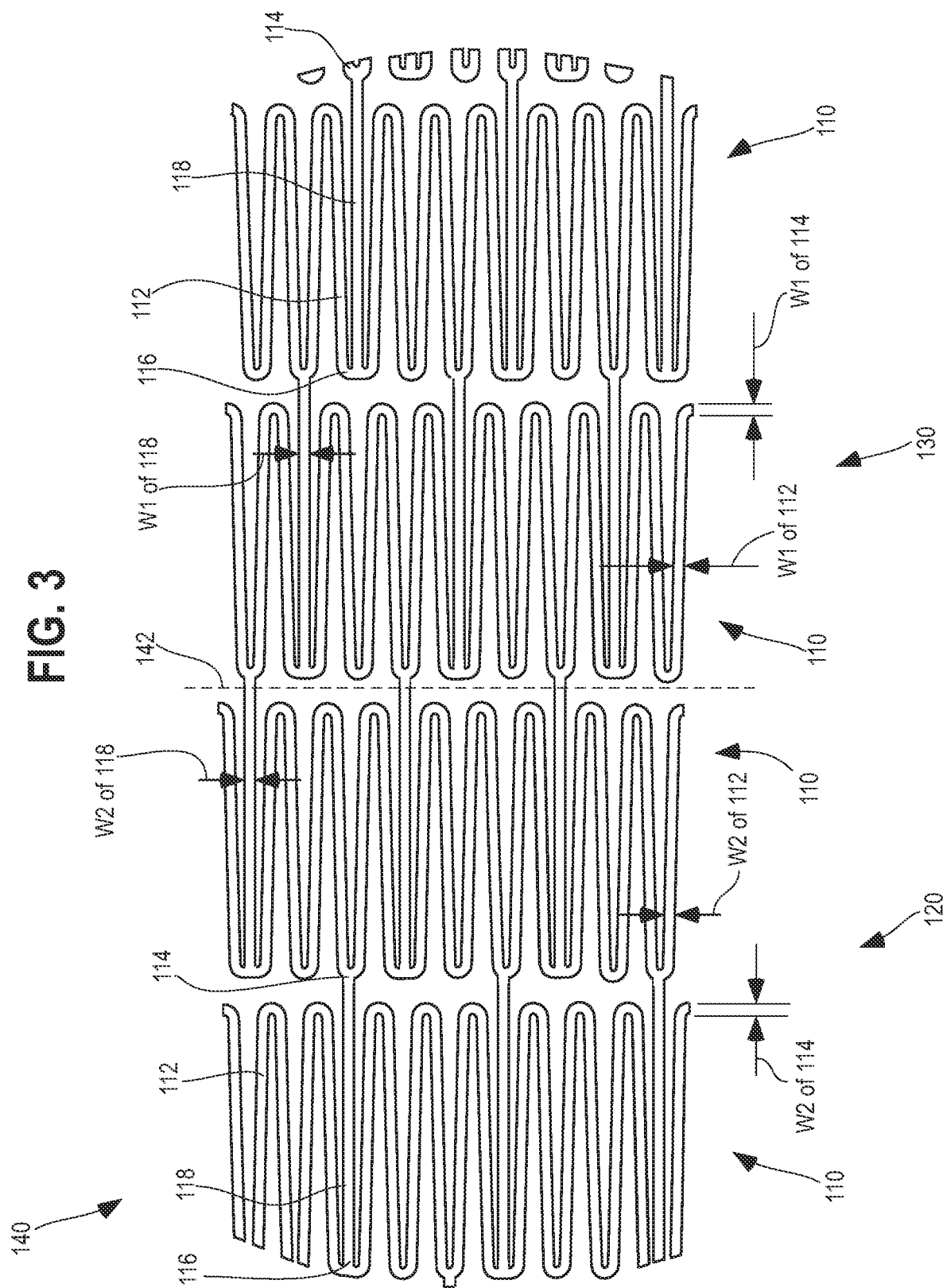
FIG. 3 illustrates exemplary strut members of the exemplary stent of FIG. 2, in accordance with various embodiments.
Figure 4:
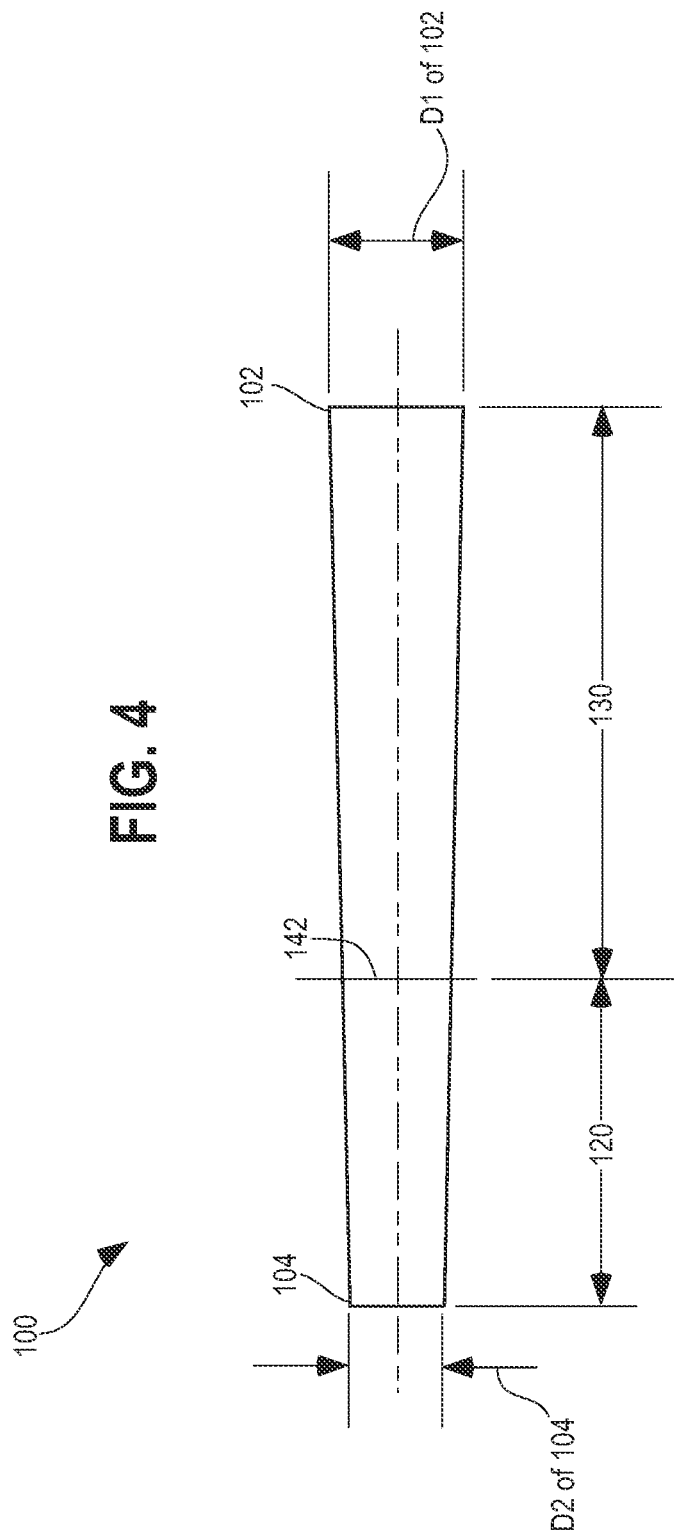
FIG. 4 illustrates an exemplary profile of the exemplary stent 100 of FIG. 2 having a distal end with a smaller diameter than the diameter of the proximal end, in accordance with various embodiments.

FIG. 2 illustrates an exemplary stent 100 comprising a distal end 104 and a proximal end 102, the distal end 104 having a greater flexibility than the proximal end 102, in accordance with various embodiments. FIG. 3 illustrates exemplary strut members 112 of the exemplary stent 100 of FIG. 2, in accordance with various embodiments. FIG. 4 illustrates an exemplary profile of the exemplary stent 100 of FIG. 2 having a distal end with a smaller diameter than the diameter of the proximal end, in accordance with various embodiments. Although FIGS. 2 and 3 may illustrate the stent 100 in a flat view, the top ends of the stent 100 would be joined with the bottom ends to form the stent 100 in a cylindrical form. Referring to FIGS. 2-4, the self-expanding cylindrical stent 100 comprises a distal end 104, a proximal end 102, and a plurality of circumferential strut segments 110. The strut segments 110 may comprise strut members 112 and longitudinal connecting members 118. The strut members 112 may be arranged in a pattern, such as a zig-zag pattern having peaks 114 and valleys 116, or any suitable pattern. The strut segments 110 may each be coupled to at least one other strut segment 110 by the longitudinal connecting members 118.

Stents are typically implemented as either an open cell stent or a closed cell stent. A closed cell stent has each peak and valley of each strut segment connected to a peak or valley of an adjacent strut segment, with the exception of the strut segments on the proximal and distal ends. Open cell stents, on the other hand, have some peaks and/or valleys that are not connected to peaks and/or valleys of adjacent strut segments. In a preferred embodiment, the stent 100 may be an open cell design, for example, to minimize the reduction in length of the stent 100 when expanding the stent 100 from a pre-deployed state to a deployed state. Moreover, an open cell stent structure has an enhanced ability to expand and conform to a non-circular cavity wall, such as the sinuses, than a closed cell structure. For example, the individual segments of an open cell stent have less dependence on neighbor segments than in a closed cell design. Accordingly, the open cell segments are better suited for conforming to irregularities of a non-circular cavity. Referring to FIG. 3, the longitudinal connecting members 118 may be arranged in a periodic peak-to-valley connection scheme, such as every third peak connected to every third valley by a longitudinal connecting member 118. Although a peak-to-valley connection scheme with a period of three is illustrated in FIG. 3, other connection schemes and periods are contemplated. For example, the connections scheme may be a peak-to-peak connection scheme, midstrut-to-midstrut connection scheme, a hybrid connection scheme, or any suitable connection scheme. As another example, the period may be two, four, variable periods, or the like. Furthermore, the longitudinal connecting member 118 may be flex connections, non-flex connections, a hybrid of flex and non-flex connections, or any suitable connections.

The stent 100 may be sized to cover the sigmoid sinus and substantially the entire transverse sinus. For example, depending on a size and height of a patient, the length of the stent may be 6-9 cm long with a mean of approximately 7 cm. The appropriately sized stent maintains patency of both sinus structures while substantially eliminating the chance of a re-collapse and substantially eliminating the possibility of a stent jail.

The stent 100 may be made of nickel titanium, also known as nitinol, or any suitable material. In the case of a nitinol stent 100, the collapsed stent 100 can be inserted into a body lumen, where body temperature warms the stent 100 and the stent 100 returns to its original expanded shape following removal of a constraining sheath as described below with reference to FIGS. 5-10.

In various embodiments, the stent 100 may comprise segments 110 of strut members 112 having different flexibility. Specifically, one or more segments 110 at the distal end 104 of the stent 100 may have a greater flexibility than one or more segments 110 at the proximal end 102 of the stent 100. For example, as illustrated in FIG. 2, the stent 100 may have a first group of flexible segments 120 and a second group of stiff segments 130. The first group of flexible segments 120 may include eight or any suitable number of segments 110 and the second group of stiff segments 130 may include fourteen or any suitable number of segments 110. The stent 100 may transition from the group of flexible segments 120 to the group of stiff segments 130 at a transition point 142 between the two groups 120, 130. FIG. 3 illustrates the detail of the transition 142 between the flexible segments 120 and stiff segments 130. Additionally and/or alternatively, the segments 110 of the stent 100 may progressively increase in stiffness from the distal end 104 to the proximal end 102 of the stent 100. For example, each segment 110 may have the same or more flexibility than the adjacent segment 110 in the proximal end 102 direction.

In a representative embodiment, the flexibility of a segment 110 may correspond with the radial outward expansion strength (RES) of that segment 110. For example, the group of flexible segments 120 may have a lower RES than the group of stiff segments 130. Accordingly, if placing the stent in the venous sinuses, the group of flexible segments 120 having the low RES at the distal end 104 of the stent 100 may scaffold and hold open the transverse sinus region while not exerting too much pressure to the dura inner lining. The group of stiff segments 130 at the proximal end of the stent 100 and having an RES greater than the flexible segments 120 are positioned in the sigmoid region that can contain excessive arachnoid granulation ingrowth and/or stenosis that may require more force to open and restore better blood outflow. The low RES distal end 104 of the stent 100 transitioning to a higher RES proximal end 102 may translate to a more flexible and integral transition within the stent delivery system 200. Specifically, the integration of the stent 100 in the stent delivery system 200 provides a faster and easier delivery of the stent 100 by improving the ability to navigate the sigmoid junction, as described below with reference to FIG. 9, for example.

In various embodiments, the amount of RES and flexibility of portions of the stent 100 may be constructed based on the distance between stent segments 110 and/or the length of the longitudinal connecting members 118, the number of longitudinal connecting members 118, the amount of strut members 112, and/or the width of the strut members 112 and/or the longitudinal connecting members 118. For example, a greater distance between stent segments 110 and/or longer longitudinal connecting member 118 may correspond with a lower RES and greater flexibility. As another example, a larger number of longitudinal connecting members 118 may correspond with a higher RES and greater stiffness. Furthermore, a greater amount of strut members 112 may correspond with a higher RES and larger stiffness. Additionally, a narrower width of the strut members 112 and/or the longitudinal connecting members 118 may correspond with a lower RES and greater flexibility. For example, referring to FIG. 3, the widths of the strut members 112, strut member peaks 114, and longitudinal members 118 in the group of stiff segments 130 are referred to as W1. The widths of the strut members 112, strut member peaks 114, and longitudinal members 118 in the group of flexible segments 120 are referred to as W2. The widths W1 in the group of stiff segments 130 may be greater than the widths W2 in the group of flexible segments 120. As an example, the width W1 of the strut members 112 and longitudinal members 118 in the group of stiff segments 130 may be approximately 0.0050 inches and the width W1 of the strut member peaks 114 may be approximately 0.0065 inches. In the group of flexible segments 120, the width W2 of the strut members 112 and the longitudinal connecting members 118 may be approximately 0.0045 inches and the width W2 of the strut member peaks 114 may be approximately 0.0060 inches. In certain embodiments, the approximately 10 percent reduction in width W2 may correspond with a reduction in stiffness by approximately 33 percent of the group of flexible segments 120 compared to the group of stiff segments 130.

Referring to FIG. 4, the stent 100 may be conically shaped or stepped such that the lumen diameter D1/D2 of the stent 100 is greater at the proximal end 102 than at the distal end 104. FIG. 4, for example, illustrates a profile of a cylindrical stent 100 that is conically shaped and includes a greater lumen diameter D1 of the stent 100 at the proximal end 102 than the stent lumen diameter D2 at the distal end 104. Additionally and/or alternatively, the stent 100 may have a mix of straight and conical portions. For example, the stent 100 may have straight portions at the distal 104 and proximal 102 ends with a conical portion therebetween. As another example, the stent 100 may have a straight portion at the distal end 104 followed by a conical portion between the straight portion and the proximal end 102, or vice versa. The inclusion of a conical portion ensures different lumen diameters D1/D2 at the proximal 102 and distal 104 ends of the stent 100. In a representative embodiment, the proximal end 102 of the stent 100 has a greater diameter D1 than the diameter D2 at the distal end 104. For example, the diameter D1 at the proximal end 102 may be approximately 0.3937 inches and the diameter D2 at the distal end 104 may be approximately 0.2756 inches. Accordingly, if placing the stent 100 in the venous sinuses, the smaller diameter D2 at the distal end 104 of the stent may be appropriately sized for the transverse sinus region and the transition to the larger diameter D1 at the proximal end 102 of the stent 100 may be appropriately sized for the sigmoid sinus region. In that way, the contact between the strut members 112 and the dura wall of both the transverse sinus region and the sigmoid sinus region may be maximized so that portions of the stent 100 are not left free in the open blood flow of the lumen of the venous sinuses.

Figure 5:
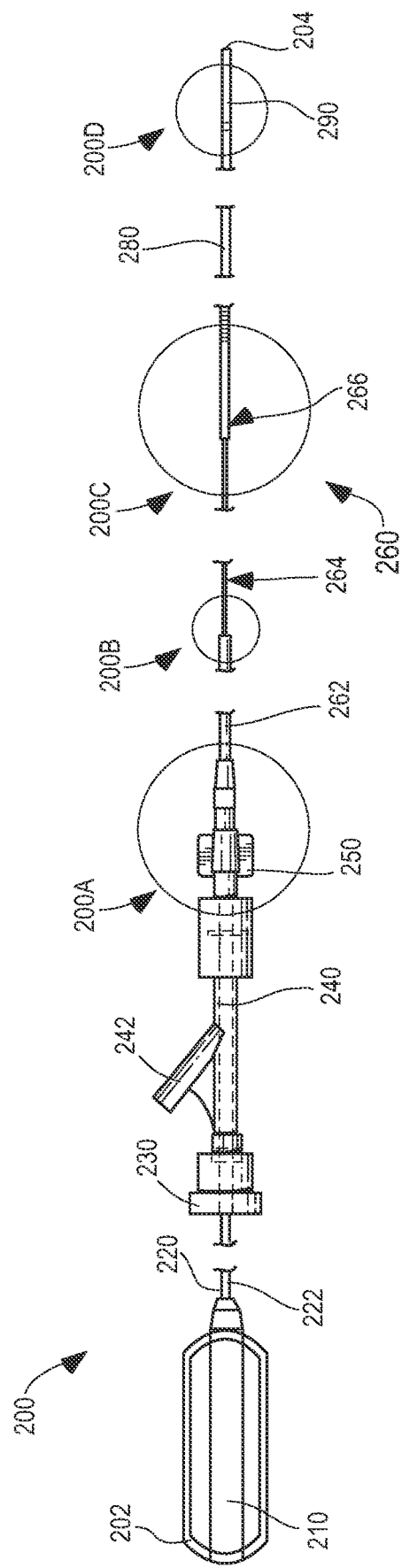
FIG. 5 illustrates an exemplary stent delivery system, in accordance with various embodiments.

FIG. 5 illustrates an exemplary stent delivery system 200, in accordance with various embodiments. FIG. 6 illustrates a detail view of portions 200A, 200B, 200C, 200D of the exemplary stent delivery system 200 of FIG. 5, in accordance with various embodiments. FIG. 7 illustrates a detail view of an inner portion 200E of the stent delivery system 200 of FIG. 5, in accordance with various embodiments. FIG. 8 illustrates a detail view of an outer portion 200F of the stent delivery system 200 of FIG. 5, in accordance with various embodiments. FIG. 9 illustrates an exploded, cross-sectional view of the inner portion 200E of the stent delivery system 200, the stent 100, and the outer portion 200F of the stent delivery system 200, where the increasing flexibility of the stent delivery system 200 with the stent 100 from the proximal end 102, 202 toward the distal end 104, 204 of the system 200 and stent 100 is illustrated by a mapping to an exemplary flexibility chart 300, in accordance with various embodiments.

Referring to FIGS. 5-9, a stent delivery system 200 may comprise an outer portion 200F and an inner portion 200E extending between a proximal end 202 and a distal end 204 of the system 200.

The inner portion 200E of the stent delivery system 200 may comprise a delivery handle 210 at the proximal end 202, a delivery tip 290 at the distal end 204, and a shaft 220 extending from the delivery handle into the delivery tip 290. The shaft 220 may comprise a proximal portion of the shaft 222 that connects to the delivery handle 210, a central portion of the shaft 224, and a distal portion of the shaft 226 that includes and/or extends through a push coil 270 and a stent bed 280. In various embodiments, the shaft portions 222, 224, 226, 270, 280 may be tubular structures that are made of different materials and/or may have different outer diameters, for example, to increase flexibility from the proximal end 202 along a longitudinal axis to the distal end 204. For example, the proximal portion of the shaft 222 attached to the delivery handle and the central portion of the shaft 224 may be a hypotube or any suitable tube having a first diameter. The distal portion of the shaft 224 may have a second diameter that is less than the first diameter of the proximal 222 and central 224 portions and/or may include sections made of different materials such as a coiled section 270.

The stent bed 280 may be the portion of the distal shaft 226 between the push coil 270 and the delivery tip 290. The stent bed 280 may be a thin wall polyimide tube having a constant stiffness. The stent bed 280 may extend through a lumen in a pre-deployed stent 100 such that the pre-deployed stent 100 is positioned and carried on the stent bed 280 until deployment. The pre-deployed stent 100 positioned on the stent bed 280 may be held in a pre-deployed state by sheathing 260 that is slidable over the stent 100 as described below. In various embodiments, the proximal and/or distal ends of the stent bed 280 may include one or more markers, such as radio-opaque markers, to enhance visualization of the location of the pre-deployed stent 100 within the stent delivery system 200. For example, an operator of the stent delivery system 200 may monitor the navigation of the system 200 via medical image data, such as fluoroscopic images, ultrasound images, or images of any suitable medical imaging modality. The marker(s) may be readily identifiable in the image data to assist the operator in accurately positioning the stent delivery system 200 in the stent zone.

The push coil 270 may be a portion of the distal shaft 226 at a proximal end of the stent bed 280. Additionally and/or alternatively, the push coil 270 may be arranged concentrically between the distal shaft 226 and the sheathing 260. The push coil 270 may act as a stop for a stent 100 positioned on the stent bed 280 by preventing the pre-deployed stent 100 from sliding from the stent bed 280 toward the proximal end 202. In various embodiments, the push coil 270 may have a greater flexibility at a distal end of the coil 270 than at the proximal end of the coil 270. For example, the push coil 270 may have a plurality of sections, where each of the sections has an increased flexibility from the proximal end of the coil 270 along a longitudinal axis to the distal end of the coil 270.

The delivery tip 290 may comprise a distal end 294 and a proximal end 292. The delivery tip 290 may comprise a lumen configured to allow a guidewire 269 to pass through the delivery tip 290 such that the stent delivery system may glide over the guidewire 290 during navigation of the system to the stent zone in the venous sinuses or other body lumen. The delivery tip 290 may comprise a tip transition 296 at the proximal end 292 of the delivery tip 290. The tip transition 296 may have a larger outer diameter configured to prevent the sheathing 260 of the outer portion 200F of the stent delivery system 200 from sliding distally over the delivery tip 290. In a representative embodiment, the delivery tip 290 may be made of a medical grade polymer, e.g., polyether block amide, such as PEBAX, and may have a durometer of approximately 35.

In various embodiments, the stent delivery system 200 may include a rapid exchange junction 268 through the sheathing 260 and into the distal shaft portion 226. The guidewire 269 runs within a guidewire lumen in the stent delivery system 200 from the lumen in the delivery tip 290 at the distal end 204 of the system 200 to a point where the guidewire lumen terminates on the outside of the system 200 at the rapid exchange junction 268 at the distal shaft portion 226 and distal sheathing portion 266 that is proximal the push coil 270. The rapid exchange junction 268 may facilitate the rapid placement of the stent delivery system 200 over the guidewire 269 and allow for the use of shorter guidewires than used in over-the-wire catheter systems.

The outer portion 200F of the stent delivery system 200 may comprise a hub 230, 240, 250 and sheathing 260. The hub may comprise a lock 230, a Tuohy Borst valve 240, and a Luer wing 250. The lock 230 may be, for example, a standard Luer lock or any suitable lock for connecting the Tuohy Borst valve 240 to the proximal portion 222 of the shaft 220. The lock 230 may be loosened to allow the hub 230, 240, 250 and sheathing 260 to slide over the shaft 220 and may be tightened to prevent such movement. The Tuohy Borst valve (also known as a hemostasis valve) 240 may be attached to the lock 230 at a proximal end and may be coupled to a Luer wing 250 at a distal end. The Tuohy Borst valve 240 may receive the internally inserted shaft 220 that can move within the valve 240 in a direction parallel to its longitudinal axis. The Tuohy Borst valve 240 may include a Luer port 242 for securing the valve 240 to other medical instruments and devices that may be used during a procedure to deliver a stent 100 to the stent zone within a patient. The Luer wing 250 may securely attach to the sheathing 260. The shaft 220 is configured to extend through the lock 230, Tuohy Borst valve 240, Luer wing 250, and sheathing 260.

The sheathing 260 may include a proximal portion 262 terminating at the Luer wing 250, a distal portion 266 terminating at the tip transition 296 at the proximal end 292 of the delivery tip 290, and a central portion 264 between the proximal 262 and distal 266 portions. In various embodiments, the sheathing portions 262, 264, 266 may be tubular structures that are made of different materials and/or may have different outer diameters, for example, to increase flexibility from the proximal end 202 along a longitudinal axis to the distal end 204. The sheathing 260 is configured to slide longitudinally over the shaft 220 and stent 100 between a pre-deployed position and a deployed position. For example, in a pre-deployed position, the sheathing 260 extends over the pre-deployed stent 100 to the tip transition 296 of the delivery tip 290. After the stent delivery system 200 is navigated to the stent zone, the sheathing 260 may be pulled back over the stent 100 by releasing lock 230 and pulling the hub 230, 240, 250 toward the delivery handle 210 at the proximal end 202 of the system 200. The stent 100 deploys by expanding as the sheathing 260 passes over and releases the stent 100 from its pre-deployed compressed state. In various embodiments, the sheathing 260 may comprise one or more markers, such as radio-opaque markers, to enhance visualization in medical image data of the location of the pre-deployed stent 100 within the stent delivery system 200. In a representative embodiment, the distal portion 266 of the sheathing 260 may be made of a medical grade polymer, e.g., polyether block amide, such as PEBAX. In an exemplary embodiment, the distal portion 266 of the sheathing 260 may include a most distal section 266a having a flexible durometer of approximately 35, a central section 266b having a semi-flexible durometer of approximately 55, and a proximal section 266c having a stiff durometer of approximately 72. In this way, the stiffness of the distal portion 266 of the sheathing 260 may increase from the most distal section 266a to the proximal section 266c.

Referring to FIG. 9, a chart 300 is shown mapping the stiffness or flexibility 302 of the combined inner portion 200E of the stent delivery system 200, stent 100, and outer portion 200F of the stent delivery system 200. As shown in FIG. 9, the stiffness 302 gradually increases and/or steps up from the distal end 204 of the stent delivery system 200 having the loaded stent 100 toward the proximal end 202 of the system 200. For example, the delivery tip may have a durometer of approximately 35. As shown in FIG. 9, the delivery tip 290 portion of the stent delivery system 200 may be the most flexible 302. The next section in the proximal direction from the delivery tip 290 is the stent bed 280 loaded with the stent 100 and a section of the distal portion of the sheathing 266. The distal portion 266 of the sheathing 260 may have a most distal section 266a having a flexible durometer of approximately 35. Accordingly, the combination of the distal portion 266 of the sheathing with the stent bed 280 and the flexible group of segments 120 of the stent 100 may have a greater stiffness 302 than the delivery tip 290. Continuing in the proximal direction, the stiffness 302 of the combination of the most distal section 266a of the distal portion of the sheathing 266, the stiff group of segments 130 of the stent 100, and the stent bed 280 increases due to the stiffer group of segments 130 of the stent 100.

The central section 266b of the distal portion 266 of the sheathing may have a semi-flexible durometer of approximately 55 and the proximal section 266c may have a stiff durometer of approximately 72. The push coil 270 may have a flexible section 272 with loose windings and a stiff section 274 having tight windings. Consequently, the stiffness 302 continues to increase for the combination of the flexible section 272 of the coil 270 and the central section 266b of the distal portion of the sheathing 266. In the same way, the stiffness 302 steps up for the combination of the stiff section 274 of the coil and the central section 266b of the distal portion of the sheathing 266.

The distal shaft portion 226 in the proximal direction from the coil 270 may have a greater stiffness than the coil. Accordingly, the stiffness 302 of the stent delivery system 200 having the loaded stent 100 may step up again for the combined system components including the distal shaft portion 226 in the proximal direction from the coil 270 and the proximal section 266c of the distal portion 266 of the sheathing 260.

In summary, not only does the different materials and the different durometer of the individual components effect the flexibility of the stent delivery system 200 having the loaded stent 100, but the combination of components along the longitudinal axis of the system 200 loaded with the stent 100 provides a gradual increase in of stiffness 302 from the distal end 204 toward the proximal end 202 of the system 200 in a new way that improves control and navigation of the system 200 for delivering the stent 100.

Figure 10:
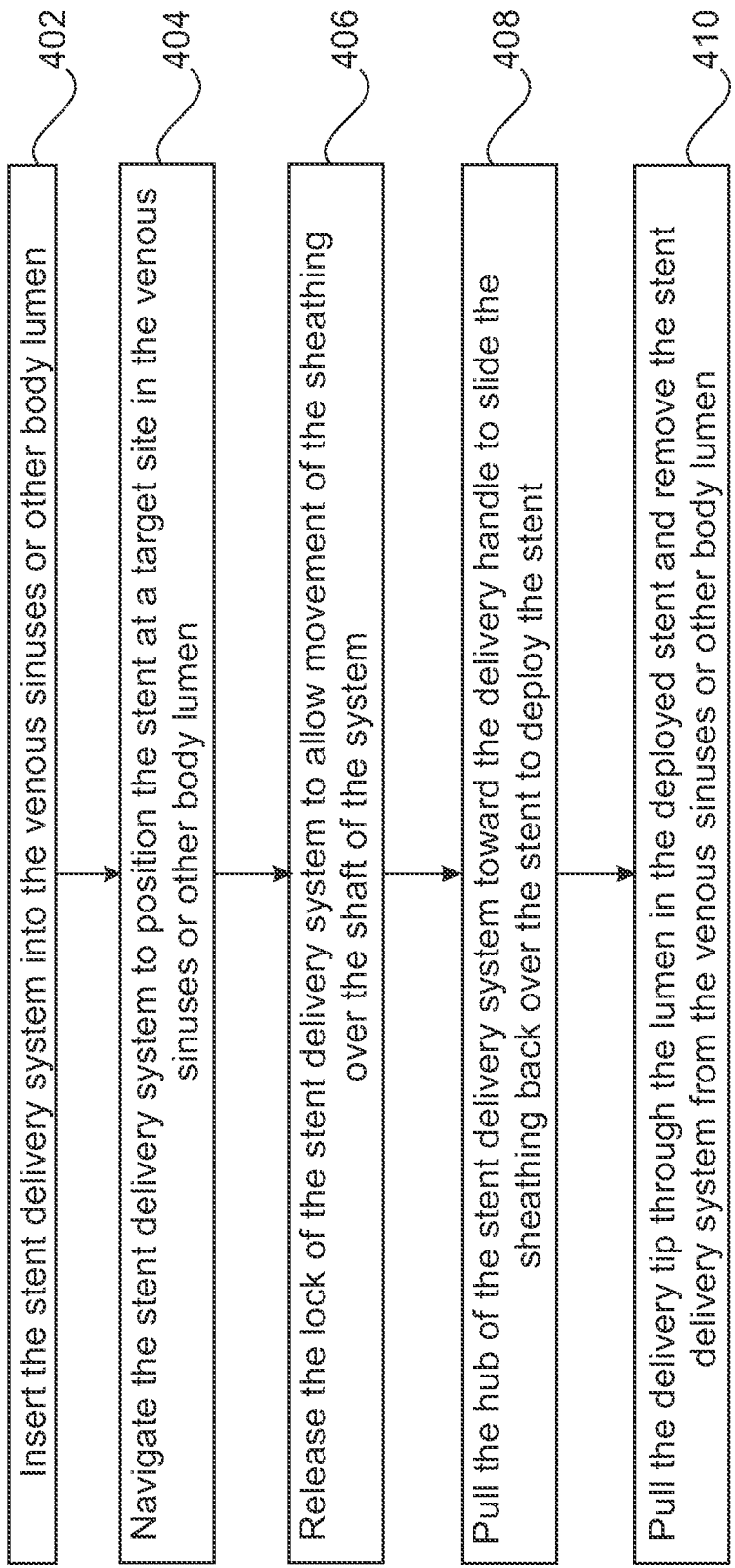
FIG. 10 is a flow chart illustrating exemplary steps that may be utilized for providing enhanced navigation of a stent delivery system for placement of a stent, in accordance with various embodiments.

FIG. 10 is a flow chart 400 illustrating exemplary steps 402-410 that may be utilized for providing enhanced navigation of a stent delivery system 200 for placement of a stent 100, in accordance with various embodiments. Referring to FIG. 10, there is shown a flow chart 400 comprising exemplary steps 402 through 410. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a stent delivery system 200 may be inserted into the venous sinuses or other body lumen. For example, the stent delivery system 200 may access the venous sinuses at the sigmoid junction via the jugular vein. The stent delivery system 200 may include a collapsed, pre-deployed stent 100 carried between a shaft 220 and/or stent bed 280 and sheathing 260 near the distal end 203 of the system 200. In various embodiments, the stent 100 may be made of nitinol. The insertion of the stent delivery system 200 into the venous sinuses or other body lumen provides body temperature that warms the nitinol stent 100, which allows the stent 100 to return to its original expanded shape after a sheath 260 of the system is removed at step 408.

At step 404, the stent delivery system 200 is navigated to position the stent 100 at a target site in the venous sinuses or other body lumen. For example, the stent delivery system 200 may access the venous sinuses via the jugular vein, through the sigmoid junction and sigmoid sinus, and into transverse sinus. The target site, or stent zone, for placement of the stent 100 may span from substantially the distal end of the transverse sinus into the sigmoid sinus. The navigation of the stent delivery system 200 having the stent 100 includes traversing the tortuous sigmoid junction. Accordingly, in various embodiments, both the stent 100 and the stent delivery system 200 may have a flexibility that increases from the proximal end 102, 202 of the stent 100 and catheter 200 to the distal end 104, 204 of the stent 100 and catheter 200. This progressive change in flexibility provides increased maneuverability at the distal end 104, 204 while providing the stiffness to control the system 200 toward the proximal end 102 of the system 200.

At step 406, the lock 230 of the stent delivery system 200 is released to allow movement of the sheathing 260 over the shaft 220 of the system 200. For example, lock 230 may be unscrewed or otherwise loosened from the shaft 220.

At step 408, the catheter hub 230, 240, 250 may be pulled toward the delivery handle 210 to slide the sheathing 260 back over the stent 100 to deploy the stent 100. For example, the sheathing may be attached to the catheter hub 230, 240, 250 at the Luer wing 250 such that when the hub 230, 240, 250 is pulled over the shaft 220, the sheathing 260 moves with the hub 230, 240, 250.

At step 410, the delivery tip 290 may be pulled through the lumen in the deployed stent 100 and the stent delivery system 200 may be removed from the venous sinuses or other body lumen. For example, the removal of the sheathing 260 at step 408 may deploy the collapsed stent 100 to an expanded state that opens the stent lumen. Accordingly, the delivery tip 290 of the stent delivery system 200 may pass through the opened stent lumen as the stent delivery system 200 is pulled back through and out of the venous sinuses or other body lumen to remove the stent delivery system 200 from the patient.

Aspects of the present invention provide a stent delivery system 200. In accordance with various embodiments, the stent delivery system 200 comprises a delivery handle 210 at a proximal end 202 of the stent delivery system 200, a catheter hub 230, 240, 250, a delivery tip 290 at a distal end 204 of the stent delivery system 200, a shaft 220, a stent 100, and sheathing 260. The delivery tip 290 comprises a tip distal end 294 and a tip proximal end 292. The delivery tip 290 has a first flexibility. The shaft 220 extends from the delivery handle 210 through the catheter hub 230, 240, 250 and into the delivery tip 290. The shaft 220 comprises a coil 270 and a stent bed 280. The coil 270 comprises a coil distal end and a coil proximal end. The stent bed 280 is between the coil distal end and the tip proximal end 292. The stent 100 is loaded on to the stent bed 280 and comprises a stent distal end 104, a stent proximal end 102, and a cylindrical body between the stent distal end 104 and the stent proximal end 102. A first portion 120 of the cylindrical body at the stent distal end 104 has a greater flexibility than a second portion 130 of the cylindrical body at the stent proximal end 130. The sheathing 260 is coupled to the catheter hub 230, 240, 250 and movable over the stent bed 280 between pre-deployed and deployed positions. The sheathing 260 extends over the stent bed 280 if in the pre-deployed position. The sheathing 260 is pulled back from the stent bed 280 if in the deployed position. The stent 100 is compressed by the sheathing 260 on the stent bed 280 if in the pre-deployed position. The stent 100 expands if the sheathing 260 is pulled back from the stent bed 280 in the deployed position. The sheathing 260 comprises a sheathing distal end and a sheathing proximal end. The sheathing 260 comprises a flexible section 266a at the sheathing distal end, a semi-flexible section 266b adjacent the flexible section 266a, and a stiff section 266c adjacent the semi-flexible section 266b. The combination of the stent bed 280, the first portion 120 of the cylindrical body of the stent 100, and the flexible section 266a of the sheathing 260 has a second flexibility that is less than the first flexibility. The combination of the stent bed 280, the second portion 130 of the cylindrical body of the stent 100, and the flexible section 266a of the sheathing 260 has a third flexibility that is less than the second flexibility.

In various embodiments, the coil 270 comprises a loose wound region 272 at the coil distal end having a greater flexibility than a tight wound region 274 of the coil 270 at the coil proximal end. In certain embodiments, the combination of the loose wound region 272 of the coil 270 and the semi-flexible section 266a of the sheathing 260 has a fourth flexibility that is less than the third flexibility. In a representative embodiment, the combination of the tight wound region 274 of the coil 270 and the semi-flexible section 266b of the sheathing 260 has a fifth flexibility that is less than the fourth flexibility. In various embodiments, the combination of the tight wound region 274 of the coil 270 and the stiff section 266c of the sheathing 260 has a sixth flexibility that is less than the fifth flexibility. In certain embodiments, the shaft 220 adjacent the coil 270 at the coil proximal end in combination with the stiff section 266c of the sheathing 260 has a seventh flexibility that is less than the sixth flexibility.

In a representative embodiment, one or more of the delivery tip 290 and the sheathing 260 is made of a medical grade polymer, e.g., polyether block amide. In various embodiments, the stent bed 280 is a thin wall tube having a constant stiffness. In certain embodiments, the delivery tip 290 has a durometer of approximately 35. In a representative embodiment, one or more of the flexible section 266a of the sheathing 260 has a durometer of approximately 35, the semi-flexible section 266b of the sheathing 260 has a durometer of approximately 55, and the stiff section 266c of the sheathing 260 has a durometer of approximately 72.

Various embodiments provide a stent 100 comprising a distal end 104 having a first diameter D2, a proximal end 102 having a second diameter D1 that is greater than the first diameter D2, and a cylindrical body between the distal end 104 and the proximal end 102. The cylindrical body comprises circumferential strut segments 110 and longitudinal connecting members 118. Each of the circumferential strut segments 110 comprises strut members 112 arranged in a pattern. Each of the circumferential strut segments 110 is connected to at least one other of the circumferential strut segments 110 by a portion of the longitudinal connecting members 118. A first plurality of the circumferential strut segments 120 at the distal end 104 of the stent 100 has a greater flexibility than a second plurality of the circumferential strut segments 130 at the proximal end 102 of the stent 100.

In certain embodiments, the first plurality of the circumferential strut segments 120 at the distal end 104 of the stent 100 has a lower radial outward expansion strength than the second plurality of the circumferential strut segments 130 at the proximal end 102 of the stent 100. In a representative embodiment, at least a portion of the cylindrical body is conically-shaped. In various embodiments, the longitudinal connecting members 118 are arranged as an open cell design. In certain embodiments, the cylindrical body is made of nickel titanium. In a representative embodiment, the cylindrical body is 6 to 9 centimeters long.

In various embodiments, the pattern of the strut members 112 is a zig zag pattern having peaks 114 and valleys 116. In certain embodiments, the longitudinal connecting members 118 are arranged in a periodic peak-to-valley connection scheme. In a representative embodiment, a first width W2 of one or both of the strut members 112 and the longitudinal connecting members 118 of the first plurality of the circumferential strut segments 120 at the distal end 104 of the stent 100 is less than a second width W1 of one or both of the strut members 112 and the longitudinal connecting members 118 of the second plurality of the circumferential strut segments 130 at the proximal end 102 of the stent 100. In various embodiments, the first plurality of the circumferential strut segments 120 at the distal end 104 of the stent 100 is 8 circumferential strut segments 110 and the second plurality of the circumferential strut segments 130 at the proximal end 102 of the stent 100 is 14 circumferential strut segments 110.

As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, a structure that is "configured" to or "operable" to perform a function requires that the structure is more than just capable of performing the function, but is actually made to perform the function, regardless of whether the function is actually performed.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method comprising:
   inserting a stent delivery system into venous sinuses, the stent delivery system comprising:
   a delivery handle at a proximal end of the stent delivery system;
   a catheter hub;
   a delivery tip at a distal end of the stent delivery system, wherein the delivery tip comprises a tip distal end and a tip proximal end, and wherein the delivery tip has a first flexibility;
   a shaft extending from the delivery handle through the catheter hub and into the delivery tip, wherein the shaft comprises a coil and a stent bed, the coil having a coil distal end and a coil proximal end, the stent bed between the coil distal end and the tip proximal end;
   a stent loaded on to the stent bed, wherein the stent comprises a stent distal end, a stent proximal end, and a body between the stent distal end and the stent proximal end, the body defining a lumen extending through the stent from the stent distal end to the stent proximal end in a deployed state, and wherein a first portion of the body at the stent distal end has a greater flexibility than a second portion of the body at the stent proximal end; and
   sheathing coupled to the catheter hub and moveable over the stent bed between pre-deployed and deployed positions, wherein the sheathing extends over the stent bed if in the pre-deployed position, wherein the sheathing is pulled back from the stent bed if in the deployed position, wherein the stent is compressed by the sheathing on the stent bed if in the pre-deployed position, wherein the stent expands if the sheathing is pulled back from the stent bed in the deployed position, wherein the sheathing comprises a sheathing distal end and a sheathing proximal end, and wherein the sheathing comprises a flexible section at the sheathing distal end, a semi-flexible section adjacent the flexible section, and a stiff section adjacent the semi-flexible section,
   wherein the combination of the stent bed, the first portion of the body of the stent, and the flexible section of the sheathing has a second flexibility that is less than the first flexibility, and
   wherein the combination of the stent bed, the second portion of the body of the stent, and the flexible section of the sheathing has a third flexibility that is less than the second flexibility;
   navigating the stent delivery system to position the stent at a target site in the venous sinuses, wherein the target site spans from a distal end of the transverse sinus into a sigmoid sinus;
   deploying the stent at the target site by pulling the sheathing back over the stent; and
   removing the stent delivery system from the venous sinuses by pulling the delivery tip through the lumen in the stent and out of the venous sinuses.

2. The method according to claim 1, wherein the stent delivery system accesses the venous sinuses at a sigmoid junction via a jugular vein.

3. The method according to claim 1, wherein the navigating the stent delivery system includes traversing a sigmoid junction.

4. The method according to claim 1, comprising releasing a lock of the stent delivery system to allow movement of the sheathing.

5. The method according to claim 1, wherein deploying the stent comprises pulling the catheter hub toward the delivery handle to slide the sheathing back over the stent.

6. The method according to claim 1, wherein the coil comprises a loose wound region at the coil distal end having a greater flexibility than a tight wound region of the coil at the coil proximal end.

7. The method according to claim 6, wherein the combination of the loose wound region of the coil and the semi-flexible section of the sheathing has a fourth flexibility that is less than the third flexibility.

8. The method according to claim 7, wherein the combination of the tight wound region of the coil and the semi-flexible section of the sheathing has a fifth flexibility that is less than the fourth flexibility.

9. The method according to claim 8, wherein the combination of the tight wound region of the coil and the stiff section of the sheathing has a sixth flexibility that is less than the fifth flexibility.

10. The method according to claim 9, wherein the shaft adjacent the coil at the coil proximal end in combination with the stiff section of the sheathing has a seventh flexibility that is less than the sixth flexibility.

11. The method according to claim 1, wherein:
    the stent distal end comprises a first diameter;
    the stent proximal end comprises a second diameter that is greater than the first diameter; and
    the body comprises circumferential strut segments and longitudinal connecting members, each of the circumferential strut segments comprising strut members arranged in a pattern, and each of the circumferential strut segments connected to at least one other of the circumferential strut segments by a portion of the longitudinal connecting members, wherein a first plurality of the circumferential strut segments at the stent distal end has a greater flexibility than a second plurality of the circumferential strut segments at the stent proximal end.

12. The method according to claim 11, wherein the first plurality of the circumferential strut segments at the stent distal end has a lower radial outward expansion strength than the second plurality of the circumferential strut segments at the stent proximal end.

13. The method according to claim 11, wherein at least a portion of the body is conically-shaped.

14. The method according to claim 11, wherein the longitudinal connecting members are arranged as an open cell design.

15. The method according to claim 11, wherein the body comprises nickel titanium.

16. The method according to claim 11, wherein the body is 6 to 9 centimeters long.

17. The method according to claim 11, wherein one or both of:
- the pattern of the strut members is a zig zag pattern having peaks and valleys, or
- the longitudinal connecting members are arranged in a periodic peak-to-valley connection scheme.

18. The method according to claim 11, wherein a first width of one or both of the strut members and the longitudinal connecting members of the first plurality of the circumferential strut segments at the stent distal end is less than a second width of one or both of the strut members and the longitudinal connecting members of the second plurality of the circumferential strut segments at the stent proximal end.

19. The method according to claim 11, wherein the first plurality of the circumferential strut segments at the stent distal end is 8 circumferential strut segments and the second plurality of the circumferential strut segments at the stent proximal end is 14 circumferential strut segments.

* * * * *